United States Patent [19]

Yone et al.

[11] Patent Number: 5,075,236

[45] Date of Patent: Dec. 24, 1991

[54] METHOD OF DETECTING KAWASAKI DISEASE USING ANTI-TUMOR NECROSIS ANTIBODY

[75] Inventors: Kenji Yone, Hino; Jun Suzuki, Tokyo; Noriyuki Tsunekawa, Hino; Arata Kato, Sayama; Satoshi Nakamura, Hino; Tsukio Masegi, Hino; Kazuo Kitai, Hino; Yataro Ichikawa, Tokorozawa, all of Japan

[73] Assignee: Teijin Limited, Osaka, Japan

[21] Appl. No.: 186,078

[22] Filed: Apr. 25, 1988

[30] Foreign Application Priority Data

| Apr. 24, 1987 | [JP] | Japan | 62-100010 |
| Jul. 1, 1987 | [JP] | Japan | 62-162233 |
| Jul. 1, 1987 | [JP] | Japan | 62-162234 |
| Oct. 26, 1987 | [JP] | Japan | 62-268218 |
| Oct. 26, 1987 | [JP] | Japan | 62-268219 |

[51] Int. Cl.$^5$ ................. G01N 33/543; G01N 33/536
[52] U.S. Cl. ..................................... 436/518; 436/536; 436/540; 436/811; 436/815; 435/7.1; 435/7.94
[58] Field of Search ..................... 436/548, 518; 435/7, 435/810, 172.2, 240.27, 7.1; 935/106, 108, 110; 530/387

[56] References Cited

U.S. PATENT DOCUMENTS 4,870,163 9/1984 Rubin et al. .................. 530/413

FOREIGN PATENT DOCUMENTS 218868 4/1987 European Pat. Off. .

OTHER PUBLICATIONS

D. Pennica, "Nature", 312, 20-27 (Dec. 1984).
Liang, C. M. et al., Biochem. Biophys. Res. Comm., vol. 137, No. 2 (1986), pp. 847-854.
Meager et al., "Hybridoma" 6 (3) 305-312 (1987).
Fendly et al., "Hybridoma" 6 (4), 359-370 (1987).
Creasey et al., "Clinical Research" 35 (1), 142A (1987).
Waage et al., "Scandinavian J. Immunol." 24 (6), 739-743 (1986).
Meager et al., "Immunobiology" 175 (1-2) 83 (1987).
Yone et al., "Immunobiology" 175 (1-2) 106 (1987).
"Clinical Chemistry", 33 (11) 2024-2027 (1987).
"Chemical Abstracts", 106 (7) Col. 48416Z (1987).
Scuderi, P. et al., "The Lancet" 1364-1365, Dec. 13, 1986.
Waage, A. et al., "The Lancet" 355-357, Feb. 14, 1987.
Yamazaki, S. et al., "Japan J. Med. Sci. Biol." 39 105-118 (1986).
Meager, A. et al., "Hybridoma" vol. 6 (3) 305-311 (1987).
Hirai, M. et al., "Journal of Immunological Methods" 96 57-62 (1987).

*Primary Examiner*—Esther L. Kepplinger
*Assistant Examiner*—Toni Scheiner
*Attorney, Agent, or Firm*—Wenderoth, Lind & Ponack

[57] ABSTRACT

A method of confirming the diagnosis of Kawasaki disease in a patient which comprises assaying the patient's body fluid for the presence of elevated levels of a substance specifically bound by an anti-tumor necrosis factor monoclonal antibody.

5 Claims, 4 Drawing Sheets

```
Cla I
 ↓
TCG.ATA.ATG.GTC.AGG.TCA.TCT.TCA.CGA.ACC.CCG.AGT.GAC.AAG.CCT.GTA.GCC.CAT.GTT.GTA
    MET-Val-Arg-Ser-Ser-Ser-Arg-Thr-Pro-Ser-Asp-Lys-Pro-Val-Ala-His-Val-Val
    0   1                                    10

GCA.AAC.CCT.CAA.GCT.GAG.GGG.CAG.CTC.CAG.TGG.CTG.AAC.CGC.CGG.GCC.AAT.GCC.CTG.CTG
Ala-Asn-Pro-Gln-Ala-Glu-Gly-Gln-Leu-Gln-Trp-Leu-Asn-Arg-Arg-Ala-Asn-Ala-Leu-Leu
        20                                   30

GCC.AAT.GGC.GTG.GAG.CTG.AGA.GAT.AAC.CAG.CTG.GTA.CCA.TCA.GAG.GGC.TTG.TAC.CTC
Ala-Asn-Gly-Val-Glu-Leu-Arg-Asp-Asn-Gln-Leu-Val-Pro-Ser-Glu-Gly-Leu-Tyr-Leu
        40                                   50

ATT.TAC.TCC.CAG.GTC.CTC.TTC.AAG.GGC.CAA.GGC.TGC.CCG.TCG.ACC.CAT.GTG.CTC.CTC.ACC
Ile-Tyr-Ser-Gln-Val-Leu-Phe-Lys-Gly-Gln-Gly-Cys-Pro-Ser-Thr-His-Val-Leu-Leu-Thr
        60                                   70

CAC.ACC.ATC.AGC.CGC.ATC.GCC.GTC.TCC.TAC.CAG.ACC.AAG.GTC.AAC.CTC.CTC.TCT.GCG.ATC
His-Thr-Ile-Ser-Arg-Ile-Ala-Val-Ser-Tyr-Gln-Thr-Lys-Val-Asn-Leu-Leu-Ser-Ala-Ile
        80                                   90

AAG.AGC.CCC.TGC.CAG.AGG.GAG.ACC.CCA.GAG.CTG.GAG.GCC.AAG.CCA.TGG.TAT.GAG.CCC
Lys-Ser-Pro-Cys-Gln-Arg-Glu-Thr-Pro-Glu-Leu-Glu-Ala-Lys-Pro-Trp-Tyr-Glu-Pro
        100                                  110

ATC.TAT.CTG.GGA.GGG.GTC.TTC.CAG.CTG.GAG.AAG.GGT.GAC.CGA.CTC.AGC.GCT.GAA.ATC.AAT
Ile-Tyr-Leu-Gly-Gly-Val-Phe-Gln-Leu-Glu-Lys-Gly-Asp-Arg-Leu-Ser-Ala-Glu-Ile-Asn
        120                                  130

CGG.CCC.GAC.TAT.CTC.GAC.TTT.GCC.GAG.TCT.GGG.CAG.GTC.TAC.TTT.GGG.ATT.ATT.GCC.CTG
Arg-Pro-Asp-Tyr-Leu-Asp-Phe-Ala-Glu-Ser-Gly-Gln-Val-Tyr-Phe-Gly-Ile-Ile-Ala-Leu
        140                                  150
Hind III

TGA.TAA.GCT
***_***
```

FIG. 7

METHOD OF DETECTING KAWASAKI DISEASE USING ANTI-TUMOR NECROSIS ANTIBODY

This invention relates to a method of detecting a substance reactive with an anti-tumor necrosis factor antibody in a body fluid of a subject so as to determine the diseased condition of the subject, monoclonal antibodies which can be used in this detection method, and a detection kit for determining the diseased condition of a subject. More specifically, this invention relates to a method which comprises detecting tumor necrosis factor (TNF hereinafter) in a body fluid of a subject by using an antibody specific for TNF and determining the progress of the diseased condition of the subject, anti-TNF monoclonal antibodies that can be used as antibodies specific for TNF, and a detection kit used in the detection method.

TNF was discovered as a physiologically active substance which appears in the blood in a CD-1Swiss mouse when the mouse is given Bacillus Calmette-Guerin (BCG) and 2 weeks later, endotoxin is administered to the mouse. It was reported by Carswell in 1975 [E. A. Carswell et al., Proc. Natl. Acad. Sci., U.S.A., 72, 3666 (1975)]. The amino acid sequence of this biologically active protein was determined by Aggarwal et al. in 1985 [B. B. Aggarwal et al., J. Biol. Chem. 260, 2345 (1985)].

Pennica et al., Shirai et al. and Wang et al. determined the amino acid sequence and the DNA sequence of human TNF [Pennica et al., Nature 312, 724 (1985); Shirai et al., Nature 313, 803 (1985), and Wang et al., Science 228, 149 (1985)]. Initially, TNF was exploited as a cancer therapeutic agent because of its anti-tumor activity. Recently its various physiological activities were elucidated, and its various functions in vivo have been investigated. For example, TNF has the activity of a mediator in vivo in endotoxin shock induced by bacterial infection [B. Beutler et al., Science, 229, 869 (1985)], the activity of inducing an inflammatory reaction on vascular endothelial cells [J. R. Gamble et al., Proc. Natl. Acad. Sci., U.S.A. 82, 8667 (1985), and pyrogenic activity [C. A. Dinarello et al., J. Exp. Med. 163, 14443, 1363, (1986)], and the activity of inducing another inflammatory cytokine, interleukin 1, one inflammation-causing substance [P. P. Nawroth et al., J. Exp. Med., 163, 1363 (1986)] or prostaglidins [P. R. Backwich et al., Biochem. Biophys. Res. Comm., 136, 94 (1986)].

In view of many such research results, TNF is considered to have hormone-like activity as an information transmitting substance in vivo which provokes many physiological actions. These research results therefore suggest a possibility that quantitative changes of TNF in vivo such as abnormal increases or deceases may have to do with the conditions of many diseases. The present inventors thus presumed that detection of the presence of TNF in a body fluid such as blood and measurement of its concentration would be beneficial for monitoring many diseases.

Investigations of the present inventors have shown that the body fluid of a patient contains TNF and the amount of TNF closely relates to the progress of his diseased condition; that, therfore, a change in his diseased condition, especially aggravation, can be predicted to some extent by accurately determining the concentration of TNF in the body fluid and measuring its quantitative changes; and that by performing a preventive or curative treatment before such a change or aggravation occurs, the progress of the patient's disease can be hampered and sometimes, the disease can be cured.

It has been found particularly by the investigations of the present inventors that the body fluids of patients of Kawasaki disease whose diagnosis and progress are extremely difficult to check and patients of bacterial infections contain TNF in larger quantities than those of normal healthy persons, and the concentration of TNF and its variations closely relate to the progress of these diseases. It is very important therefore in checking the progress of the diseases of such patients, to measure the concentration of TNF in the body fluids accurately and rapidly.

Kawasaki disease (infantile acute febrile mucocutaneous lymphnode syndrome: (MCLS), which was reported by Kawasaki in 1967 [T. Kawasaki, "Allergy", 16, 178 (1967)], is a disease of unknown etiology which most frequently affects infants and children under 5 years of age. The disease is mainly characterized by prolonged fever (5 days or longer), redenning and indurative edema of hands and feet, membranous desquamation from finger tips during the convalescent stage of the disease, changes in lips and oral cavity (redenning of lips, strawberry tongue, diffuse injection of oral and pharyngeal mucosa), polymorphous exanthema, bilateral conjunctival congestion, and acute nonpurulent cerival lympnhadenopathy.

Kawasaki disease has been diagnosed on the standards disclosed in T. Kawasaki, "Shonica" (Pediatrics), 26, 935 (1985). It is very difficult to diagnose definitely because its etiology is unknown and it is diagnosed as a combination of some principal conditions. In particular, the formation of coronary aneurysm in this disease is a main cause of death. It is an urgent and important problem to find out an index of the diseased condition of Kawasaki disease which may lead to prediction of the formation of such coronary aneurysm with the progress of the disease.

The present inventors have found that in patients of Kawasaki disease of a relatively serious condition which may lead to the formation of coronary aneurysm, TNF is markedly detected in the patients' body fluid (e.g., serum).

The present inventors have also found that from a body fluid (e.g., sera) of patients of bacterial infections, TNF is detected in good correspondence to changes in the amounts of white blood cells, platelets and C reactive proteins in it, and therefore that it is very significant for the diagnosis of the condition of a bacterial infection and determination of the progress of its diseased condition to measure TNF in as body fluid.

Thus, according to this invention, there is provided a method of determination of the diseased condition of a subject which comprises detecting a substance reactive with an anti-tumor necrosis factor antibody from a body fluid taken from the subject by an immunological assay using the anti-tumor necrosis factor antibody.

According to this invention, a body fluid is taken from a patient infected with a disease or a subject suspected of the disease and the content of a reactive substance contained in it which is reactive with an anti-tumor necrosis factor antibody, specifically a tumor necrosis factor (TNF), is measured. By determining this content or its changes, the progress of the diseased condition can be judged.

The present invention can be especially advantageously used to determine the diseased conditions of patients of Kawasaki diseases and bacterial infections.

The body fluid to be taken from the subject may be any liquid component which exists in a human body, and is especially desirably a blood component such as serum or plasma because of its ease of utilization. It may also be an exudate from an inflammatory site, lymph or a joint effusion or a blood component of a diseased region or its neighborhood. When the change of the amount of TNF is to be examined by measuring it a number of times, it is desirable to utilize the blood component of the peripheral blood taken by an ordinary method. But this is not limitative.

An anti-TNF antibody is used to measure the substance reactive with anti-TNF antibody in the body fluid of the subject by immunological assay. An antiserum or monoclonal antibody specific for TNF is used as the antibody. The known sandwich method is advantageously used for the immunological assay. Usually, two types of antibodies are used in the sandwich method. In the detection method of this invention, too, the anti-TNF monoclonal antibody, particularly an anti-human TNF monoclonal antibody, is preferably used as one of the two antibodies because it permits accurate and rapid detection of TNF.

The sandwich method advantageously used in the immunological assay in this invention is a known method which is frequently used to determine the very low concentration of a specific protein using antibodies, and is described, for example, in Langone, J. J. and van Vunakis, H. (eds.): Methods in Enzymlogy, Vol. 73, Immunochemical Techniques, Part B, Academic Press, New York, 1981; Nakamura, R. M. Toto, W. R. and Tucker, E. S., III (eds.): Immunoassays in the Clinical Laboratory, Alan R. Liss, New York, 1979; and Ishikawa, E., Kawai, T. and Miyai, K. (eds.): Enzyme Immunoassay, Igaku-Shoin, Tokyo, 1981.

The disease the condition of one suspected of having it, which is to be detected in accordance with this invention, may be any disease or condition in which a substance reactive with an anti-TNF, specifically TNF, is contained in the body fluid in an amount larger than that in a normal healthy person. Kawasaki disease and bacterial infections are typical examples. The content of TNF or its changes in the body fluid of subject constitute an important standard of determining the diseased condition. The method and detection kit of this invention may equally be applied to any other diseases in which the content of TNF has to do with the determination of the diseased condition. The bacterial infection denotes a diseased condition in the body caused by bacteria that have entered the body and proliferated. Bacterial infections are classified, for example, into systemic infections such as sepsis and local infections such as respiratory organ infection. Actually however, this classification is difficult because the same pathogen may induce various disease patterns. Many of these bacterial infections are characterized by rigor and shivering, fever, articular pain, muscular pain, sweating, vomitting, diarrhea, eruption and erythema and occasionally by hypotension, shock, embolus and bleeding tendency. In many cases, however, the bacterial infection has no specific condition, and a patient with a serious case of bacterial infection is sometimes difficult to diagnose.

The present invention is also useful for monitoring the diseased condition of such a bacterial infection if it has to do with the content of TNF in the body fluid. Thus, the present invention can be applied to not only Kawasaki disease and bacterial infections but also other diseases in which the amount of TNF in body fluids becomes abnormal according to changes in the diseased conditions. Examples of such other diseases include autoimmune diseases (SLE, rhumatoid arthritis), chronic inflammatory diseases (sarcoidosis, crohn disease), congenital and acquired immunodeficiencies, vascular inflammatory diseases such as desseminated intravascular coagulation and versus host disease.

The present invention provides a method for accurate and rapid detection of an anti-TNF antibody-reactive substance in a body fluid taken from a subject using an anti-TNF antibody by immunological assay, and a kit therefor.

To detect the amount of TNF in the subject accurately is necessary for accurate determination of the diseased condition of the subject. If the detection is delayed, it is likely that the time for applying the results of the detection of the hampering of progress of the disease or to the treatment of the disease will be retarded or lost. One type of the anti-human TNF monoclonal antibody is described in Japanese Laid-Open Patent Publication No. 208924/1985. The monoclonal antibody described in this patent document binds to human TNF and inhibits its activity. The patent document, however, fails to describe to what epitope of human TNF it binds.

It has been found in accordance with this invention that the use of an anti-human TNF monoclonal antibody having the following characteristics (a) to (c).

(a) It has the ability to neutralize the cytotoxic effect of human TNF on L929 cells and the inhibitory effect of human TNF on fatty acid metabolism.

(b) It recognizes eptitopes contained in the 68th (bly) to the 97th (Ile) amino acids in the amino acid sequence of human TNF.

(c) It specifically inhibits binding of human TNF to a TNF receptor.

To the best of the knowledge of the present inventors, the anti-human TNF monoclonal antibody having the characteristics (a) to (c) is novel, and has been provided for the first time by the present invention (this monoclonal antibody is abbreviated as "MCA-A" hereinafter).

According to this invention, there is also provided an anti-human TNF monoclonal antibody which recognizes epitopes contained in the 7th (Thr) to the 37th (Leu) amino acids in the amino acid sequence of human TNF (this antibody will be abbreviated as "MCA-B"). MCA-B does not neutralize the cytotoxic effect of human TNF on L929 cells or its effect of inhibiting fatty acid metabolism.

According to this invention, there is further provided an anti-human TNF monoclonal antibody which recognizes epitopes contained in the 113th (Pro) to the 127th (Glu) amino acids in the amino acid sequence of human TNF (this antibody will sometimes be abbreviated as "MCA-C"). MCA-C neither neutralizes the cytotoxic effect of human TNF on L929 cells nor its effect of inhibiting fatty acid metabolism. It neither inhibits binding of human TNF to a TNF receptor.

MCA-A, MCA-B and MCA-C are all novel monoclonal antibodies to human TNF, and can be used as at least one anti-TNF antibody in the detection method and the detection kit provided by this invention.

MCA-A is especially preferably used in view of its binding activity.

Now, the preparation of the above monoclonal antibodies to human TNF and the detection kit will be described in detail.

Preparation of Anti-TNF Antibody (1) Preparation of cells for producing anti-TNF antibody Antibody-producing cells are prepared in accordance with a conventional method by immunizing an animal with human TNF as an antigen and recovering the antibody-producing cells from the animal. Suitable animals for use in this method include mice, rats, rabbits, guinea pigs, goats, horses and bovine. The antibody-producing cells may be, for example, spleen cells, lymph node cells and peripheral blood cells.

(2) Preparation of Myeloma Cells

There is no particular restriction on the myeloma cells used in cell fusion, and cell lines from many animals such as mice, rats, rabbits and humans can be used. Preferably, the cell lines used should have drug resistance, and be such that the unfused myeloma cells cannot survive in a selective medium and only hybridoma cells can proliferate in it. A cell line having resistance to 8-azaguanine is most commonly used. It lacks hypoxanthine-guanine-phosphoribosyl transferase and cannot grow in HAT medium (hypoxanthine-aminopterin-thymidine). preferably, the cell lines used are of the "non-secreting type". Preferably, used are, for example, $P_3/X63-Ag8U1(P_3U1)$, $P_3/X63-Ag.6.5.3$, $P_3/NS1-1-Ag4-1$ and $Sp2/O-Ag14$ derived from murine myeloma cell line MOPC-21, and rat myeloma cells 210 RCY3-.Ag1.2.3.

(3) Cell fusion

Usually, 1 t $5 \times 10^7$ myeloma cells and 1 to $5 \times 10^6$ antibody-producing cells are mixed (usually in a ratio of from 1:4 to 1:10) in a culture medium, usually Eagle's minimum essential medium (MEM) or Rosewell Park Memorial Institute (RPMI)-1640 medium, and fused in the presence of a fusion promoter preferably polyethylene glycol (PEG) having an average molecular weight ob 1000 to 6000. The concentration of PEG used is usually 30 to 50%. Viruses may also be used as the fusion promoter.

(4) Selective proliferation of hybridoma cells

After the cell fusion, the cells are suitably diluted with, for example, RPMI 1640 medium containing 10% bovine fetal serum, and plated on a microtiter plate at a rate of about $10^5$ cells per well. A selective medium (such as HAT medium) is added to each well, and the cells are cultivated while properly replacing the selective medium with a fresh one. If a 8-azaguanineresistant strain is used as the myeloma cells, all unfused myeloma cells will die in about 10 in the HAT medium. Furthermore, since the antibody-producing cells are normal cells, they cannot survive for a long time in vitro. Accordingly, cells which grow after 10 to 14 days from the start of cultivation are hybridoma cells.

(5) Screening of antibody-producing hybridoma cells

Screening of the hybridoma cells may be carried out in a customary manner. For example, part of the supernatant in the well in which the hybridoma cells have grown is sampled and reacted with human TNF or fixed human TNF, and then by reaction with a second antibody labelled with, for example, an enzyme, a radioisotope, a fluorescent substance, or a light-emitting substance, the amount of labelling is measured. Thus, the presence of an anti-human TNF antibody can be assayed.

(6) Cloning

There is a possibility that two or more clone of hybridoma cells will grow in each well. Hence, cloning is carried out, for example, by a limiting dilution method and hybridoma cells producing a monoclonal antibody are obtained.

(7) Isolation of the antibody

The purest monoclonal antibody can be obtained from the supernatant obtained by cultivating the hybridoma cells in a suitable culture medium such as RPMI-1640 medium containing about 10% of bovine fetal serum.

To obtain a large quantity of the antibody, a mineral oil such as pristane (2,6,10,14-tetramethylpentadecane) is intraperitoneally administered to an animal which is the same strain as the animal from which the myeloma cells have been taken. Thereafter, the hybridoma cells are administered to the animal and grown in large quantities in vivo. Ascites tumor is formed in 10 to 18 days after the administration, and the antibody is formed in a high concentration in the serum and acsites.

Kit for Detection of Human TNF and Preparation Thereof

The monoclonal antibodies to human TNF obtained as above are utilized as at least a part of the anti-TNF antibodies used in the detection method and detection kit of the invention.

In the immunological assay, especially the sandwich method, two types of antibodies which can bind to the target antigen (e.g., protein) are generally used. In the present invention, two types of antibodies are likewise used, and the above monoclonal antibody specific for human TNF is used as at least one of the two antibodies. The two antibodies may both be monoclonal antibodies which recognize different epitopes of human TNF. Alternatively, one of the antibodies may be a monoclonal antibody to human TNF, and the other, an antiserum to human TNF.

A kit comprising two antibodies to human TNF will now be described.

An antibody (first antibody) to human TNF is fixed to a suitable insoluble solid carrier (such as a plastic container). The antibody so fixed will be referred to as the "fixed antibody" hereinafter. The surface of the insoluble solid carrier is then coated with a suitable substance (such as bovine serum albumin) in order to avoid a non-specific binding of an assay sample (e.g., serum) to be assayed.

The insoluble solid carrier to which the first antibody is fixed is contacted, and reacted, with the assay sample at a predetermined temperature for a predetermined period of time. During this time, the fixed antibody (first antibody) binds to the TNF in the assay sample. The fixed antibody is then washed with a suitable washing solution, and then a solution (e.g., aqueous solution) of an antibody (second antibody) to human TNF which antibody is labelled with a suitable labelling substance is contacted, and reacted, with TNF bound to the fixed antibody in the insoluble solid carrier at a predetermined temperature for a predetermined period of time. The carrier is washed with a suitable washing solution, and then the amount of the labelling substance which exists on the insoluble solid carrier is measured. From the measured amount, the amount of TNF in the assay sample can be calculated.

Thus, the assay kit of this invention is composed mainly of a fixed antibody obtaining by binding a first antibody to an insoluble solid carrier and a labelled second antibody. To utilize this kit efficiently, conveniently and simply, the kit is constructed by incorporating various supplements besides the antibodies. The supplements include, for example a dissolving agent for dissolving a solid reagent, a washing agent for washing the insoluble solid carrier, a substrate for measuring enzyme activity when an enzyme is used as the labelling substance for the antibody, and a reaction stopper. These supplements are normally used in kits for immunological assay reagents.

Examples of the insoluble solid carrier used in the assay kit of this invention are polymers such as polystyrene, polyethylene, polypropylene, polyesters, polyacrylonitrile, fluorine resins, crosslinked dextran and polysaccharides, paper, glass, metal, agarose and combinations of these.

The insoluble solid carrier may be in the form of, for example, a tray, a sphere, a fiber, a rod, a disc, a receptacle, a cell or a test tube.

Radioactive substances, enzymes or fluorescent substances are advantageously used as the labelling substances. Examples of the radioactive substances are $^{125}I$, $^{131}I$, $^{14}C$ and $^{3}H$. Examples of the enzymes are alkaline phosphatase, peroxidase and beta-D-galactosidase. Examples of the fluorescent substances include fluorescein isothiocyanate and tetramethyl rhodamine isothiocyanate. These are not limitative, and other labelling substances which can be applied to immunological assay may also be used. Adjuvants may also be used to increase the sensitivity of the labelling substances.

In the detection method and kit of this invention, the aforesaid anti-TNF antibodies are used as the first and second antibodies. Specifically, two types of monoclonal antibodies which will give good results in a quantitative assay system are selected from the monoclonal antibodies produced by the method described hereinabove, and used as the first and second antibodies. An anti-human TNF antiserum obtained in a customary manner from a mammal may be used as one of the first and second antibodies.

The following examples illustrate the present invention in greater detail. It should be understood however that the invention is not limited by these examples.

EXAMPLE 1

Preparation of an anti-human TNF monoclonal antibody:

Purification of an Antigen

Human TNF used in this invention was prepared by the method described in the earlier application, Japanese Patent Application No. 90087/1986 filed on Apr. 21, 1986.

Specifically, *Escherichia coli* into which a vector expressing human TNF DNA had been introduced was cultivated to induce production of human TNF protein. After harvesting, the *E. coli* cells were ruptured by ultrasonication. The resulting suspension was purified by column chromatography on DEAE-Sepharose by the method of Shirai et al. [T. Shirai, Nature, 313, 830 (1985)]. The coarsely purified product contained about 30% of TNF.

The antigen (human TNF) used in Example 1 in the present Specification was prepared by the method substantially identical with that described in Japanese Patent Application No. 90087/1986. Purification of the prepared antigen was conducted following the method described in T. Shirai, *Nature,* 313 830 (1985), page 805, right column, lines 25-36 from the bottom. The details are as follows.

Figure 7:
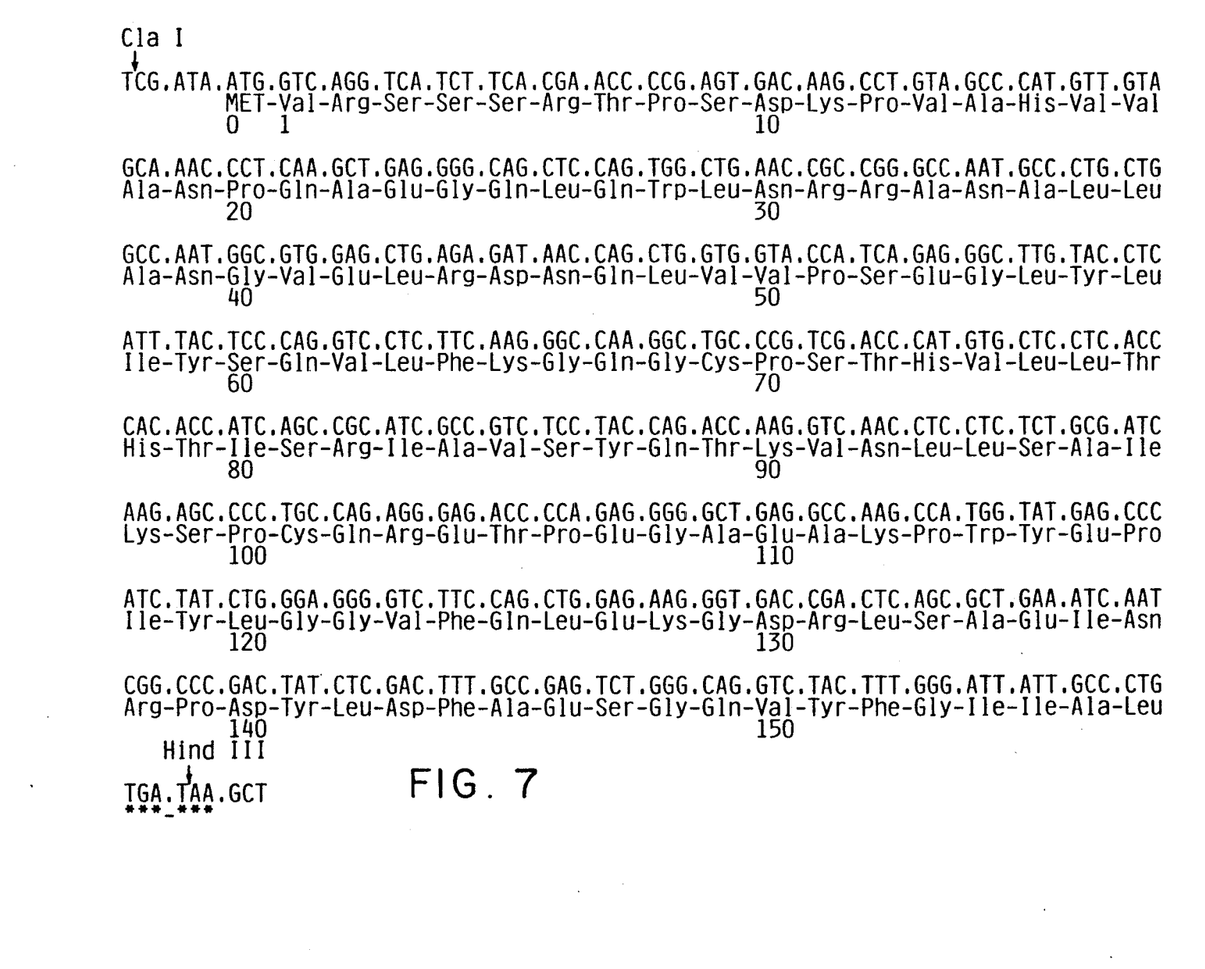
FIG. 7 shows the base sequence of the structural gene portion of human tumor necrosis factor precursor cDNA.

A. Preparation of the antigen (human TNF):

A human TNF gene having the base sequence shown in FIG. 7 was designed. The base sequence of the structural gene portion of the human TNF precursor cDNA reported by Pennica et al. [D. Pennica et al., *Nature,* 312, 724 (1984)] was used as a basis. A cleavable site by a suitable restriction endonuclease was provided at a suitable position. A translation initiation codon (ATG) was attached to the 5'-side and two translation termination condons (TGA and TAA), to the 3'-side of the human TNF gene, respectively. A cleavage site by restriction endonuclease ClaI was provided upstream of the 5'-side translation initiation codon to maintain a proper distance between the translation initiation codon and the SD sequence in a suitable condition to permit joining of a promoter. A site of cleavage with restriction endonuclease HindIII was provided downstream of the 3'-side translation termination codons to permit easy joining of a vector plasmid.

The human TNF gene designed as above was divided into 17 oligonucleotides, which were synthesized with an automated DNA synthesizer (moded 380A made by Applied Biosystems) and its 5'-terminus was phosphorylated, followed by repetitive annealing and ligation to be integrated into plasmid pBR322. The human TNF gene was thus divided into three blocks and cloned.

It was determined by the method of Maxam and Gilbert [A. M. Maxam et al., Methods Enzymol., 65, 499 (1980)] that the synthetic oligonucleotide portions of the plasmids pTNF1BR, pTNF2N and pTNF3 containing part of the human TNF gene obtained as above had the base sequences exactly as designed.

Figure 2:
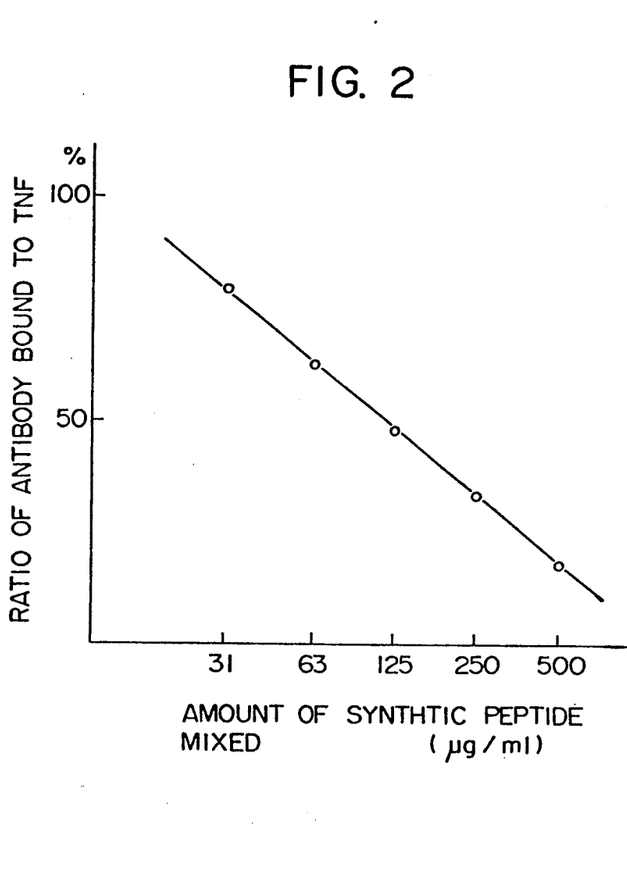
FIG. 2 shows the inhibiting effect of synthetic peptides D (see Table 2) on the binding of monoclonal antibody 1F12A7 to TNF.

From the above three plasmids, DNA fragments containing parts of the human TNF gene were recovered as shown in FIG. 2. Separately, from plasmid pYS31N containing *E. coli* trp promoter, a DNA fragment containing most of said plasmid pYS31N, was excised with restriction endonuclease ClaI and HindIII and recovered.

All of the above four were ligated and introduced into E. coli C600r-m-strain, and from the transformants, clones having the desired plasmid pTNF401NN capable of expressing the human TNF gene were selected.

Thus obtained E. coli C600r-m-strain having human TNF gene expressing plasmid pTNF401NN was inoculated in 200 ml of M9 medium containing 30 to 50 micrograms/ml of ampicillin, 0.2% of glucose and 4 mg/ml of casamino acid [in aqueous solution (pH 7.4) of 0.6% $Na_2HPL_4$-0.3% $KH_2PO_4$-0.05% NaCl-0.1% $NH_4Cl$ was sterilized in an autoclave, and an aqueous solution of $MgSO_4$ and an aqueous solution of $CaCl_2$, which had been separately sterilized in an autoclave, were added so that their final concentrations became 2 mM and 0.1 mM respectively], and cultivated with shaking at 37° C. until the $OD_{600}$ of the culture reached 0.7. Then, 3-betaindoleacrylic acid having a final concentration of 50 micrograms/ml was added to the culture broth, and the cultivation was continued further with shaking at 37° C. for 12 hours.

The E. coli cells were harvested by centrifugal separation, and washed with a PBS buffer (20 mM phosphate buffer containing 150 mM NaCl, pH 7.4). The washed cells were suspended in 10 ml of PBS buffer, and ruptured by using an ultrasonic generator (Model 200M, Kubota), and then the solid residues were removed by centrifugal separation.

This-HCl buffer (pH 6.8) SDS, 2-mercaptoethanol and glycerol were added to a portion of the resulting E. coli lysate so as to provide final concentrations of 60 mM, 2%, 4% and 10%, respectively, and SDS-polyacrylamide gel electrophoresis was performed [Suzuki, Iden (Genetics), 31, 43 (1977)]. The concentration of the separating gel was adjusted to 12.5%, and an SDS, Tris-glycine system [U.K. Laimmli, Nature, 227, 680 (1970)] was used as an electrophoretic buffer. After the electrophoresis, the proteins in the gel were stained with Coumassie Brilliant Blue R-250 (Bio-Rad), and the expression of the human TNF gene was determined.

The measurement of the activity of human TNF protein was conducted in accordance with the method of Ruff et al. [Ruff, *J. Immunol.*, 126, 235 (1981)]. That is, the E. coli lysate containing the human TNF protein was successively diluted with a medium. The resulting diluted sample (100 microliters) was mixed with 100 microliters of a suspension of mouse L-929 fibroblast cells (ATCC CCL-929) at a concentration of $4 \times 10^5$/ml, in a 96-well tissue culture microtiter plate (Coaster). In that occasion, actinomycin D (Cosmegen, Banyu Pharmaceutical Co., Ltd.) of a final concentration 1 microgram/ml was added. As the medium, Eagle's minimum essential medium (product of Nissui Seiyaku) containing 5% (vol./vol.) bovine fetal serum was used. The microtiter plate was cultivated at 37° C. for 20 hours in air containing 5% carbon dioxide gas. The, the living cells were stained with a crystal violet solution [prepared by dissolving 0.5% (wt/vol) of crystal violet in a 5% (vol/vol) aqueous solution of methanol]. The excess of the crystal violet was washed off, and the microtiter plate was dried. The remaining crystal violet was extracted with 100 microliters of 0.5% aqueous solution of SDS, and the absorbance of the extract at 595 nm was measured by an ELISA analyzer (model ETY-96, Toyo Sokki). This absorbance is proportional to the number of surviving cells. The dilution ratio of the E. coli lysate containing the human TNF protein which corresponds to 50% of the absorbance of undiluted E. coli lysate was determined from a graph (FIG. 3), and this dilution ratio is defined as one unit. It is clear from FIG. 3 that 100 microliters of the E. coli lysate containing the human TNF protein possesses the activity of $1.7 \times 10^5$ units.

B. Purification of antigen:

The E. coli lysate obtained in above section A was allowed to stand for 30 minutes at 60° C. and then centrifuged for 20 minutes at $10,000 \times g$, to provide a supernatant. The supernatant was applied to DEAE-Sepharose CL6B (Pharmacia) and eluted thoroughly with 20 mM Tris-HCl pH 8.0. The elution buffer was switched to 20 mM Tris-HCl pH 8.0-100 mM NaCl, and the eluted fraction was recovered. The fraction was dialyzed with 20 mM Tris-HCl pH 8.0, and the fraction after the dialysis was once again applied to DEAE-Sepharose CL6B. After elution the same thoroughly with 20 mM Tris-HCl pH 8.0, the elution buffer was switched to 20 mM Tris-HCl pH 8.0-150 mM NaCl and the eluted fraction was recovered. TNF content of thus purified fraction was about 30%.

Immunization of a Mouse With Human TNF

An emulsion of the above TNF fraction (50 to 100 micrograms) formed with complete Freund's adjuvant was administered to male BalB/c mice at 2-week intervals. Four days after the final immunization, the spleen was taken out for cell fusion.

Cell Fusion

Cell fusion was carried out in a customary manner. Using a mesh, a cell suspension was prepared from the spleen aseptically taken out from the immunized animal. The cell suspension was washed three times with RPMI-1640 medium, and then mixed with murine myeloma cells, P3/X63-Ag8U1 for short) [see D. E. Yelton et al., Current Topics in MIcrobiology and Immunology, 81, 1 (1978)] in a mixing ratio of from about 1:1 to 5:1, and then centrifuged. 1 ml of an RPMI-1640 solution of 50% polyethylene glycol 1540 was gradually added. The centrifuge tube was slowly stirred for 1 minute to effect cell fusion. Furthermore, RPMI-1640 medium was gradually added over an extended period of time to a final volume of 10 ml. After centrifugation, the pellets were suspended in RPMI-1640 medium containing 10% bovine fetal serum so that the number of the myeloma cells was 5 to $10 \times 10^4$ cells/0.1 ml. The suspension was plated on a 96-well microtiter plate (Costar) at a rate of 0.1 ml per well.

One day later, HAT medium was added at a rate of 0.1 ml per well, and thereafter, half of the medium was replaced by HAT medium at suitable time (day) intervals. On the 5th day and onward the growth of hybridoma cells was observed in some wells, and in two weeks, the hybridoma cells proliferated in almost all wells.

Screening and Cloning of Antibody-Producing Cells 0.1 ml of the culture supernatant was taken from the well where the hybridoma cells grew, and incubated with human TNF fixed to an immunoassay plate (Titertek), and the antibody which bound to human TNF were detected. With a probability of about 40%, there were observed wells in which antibodies having binding activity to human TNF were secreted. Only those hybridoma cells which secreted antibodies having high binding activity to human TNF were selected, plated at a density of one cell per well, and cloned by the limiting dilution method. From the clones obtained, 93 clones were selected and cultivated in RPMI-1640 containing 10% bovine fetal serum while increasing the scale from a 96-well plate, a 24-well plate, 6-well plate and finally 25 cm² flask. The culture supernatants were collected.

Each of the supernatants were mixed with human TNF solution (1000 units/ml) and incubated at 37° C. for 1 hour and then subjected to evaluation of TNF activity using L929 cells. Eleven clones having the high ability to neutralize TNF activity (9C4G5, 8E6B6, 10B7E11, 11D7G4, 8E6C6, 2B2H10, 9C4A9, 8E6D7, 1G7mD3, 8E6G4, 10B7C6) and 5 clones having the high ability to bind to TNF but hardly any ability to neutralize TNF activity (9E8G7, 1A10D4, 1F12A7, 1F12A9, P4B4D5) were selected.

Purification of Monoclonal Antibodies

The above 16 clones were further cultivated on an increasing scale using RPMI-1640 medium containing 10% bovine fetal serum, and about 500 ml to 10 liters of the culture supernatants were collected. The supernatants were stirred with 50% saturated ammonium sulfate at 4° C. for about 1 hour, and then centrifuged at 10,000 G for 30 minutes. The pellets were dissolved in a small amount of deionized water and dialyzed again at 0.1 M phosphate buffer (pH 8.0). The solution was charged on a protein A Sepharose (Pharmacia) column and the adsorbed monoclonal antibodies were eluted with 0.1 M citrate buffer (pH 5.0 or 3.0). The eluates were neutralized with sodium hydroxide and then concentrated by a membrane filter (Amicon YM-10). The buffer was replaced by 0.1 M phosphate buffer (ph 8.0) to form solutions of purified monoclonal antibodies.

EXAMPLE 2

Figure 1:
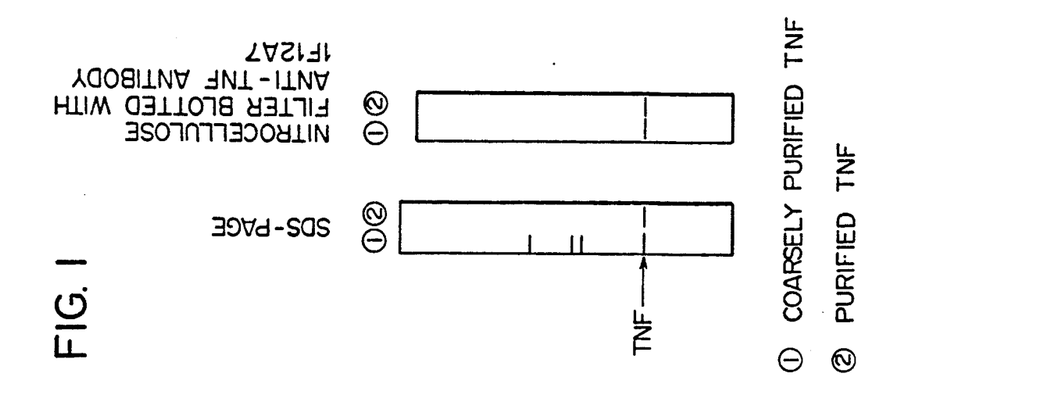
FIG. 1 shows the binding activity of an anti-TNF monoclonal antibody to TNF.

Determination of the ability to specifically recognize TNF:

The above coarsely purified TNF and purified TNF were electrophorezed on SDS-PAG PLATE 10/20 (Daiichi Chemical Co., Ltd.), and then blotted on a nitrocellulose filter in a blotting buffer (20 mM Tris, 150 mM glycine and 20% methanol). The nitrocellulose filter was shaken at room temperature for 1 to 2 hours in a buffer (20 mM Tris, 500 mM NaCl) containing 3% gelatin. The buffer was then replaced by a buffer containing 2 micrograms/ml of the purified antibody and 1% gelatin, and the nitrocellulose filter was shaken overnight at room temperature. The nitrocellulose filter was washed three times with a washing solution (20 mM Tris, 500 mM NaCl and 0.05% Tween 20). Goat anti-mouse IgG-HRP complex (Bio-Rad Company) was diluted with a buffer containing 1% gelatin to the dilution ratio specified by the manufacturer, and the microcellulose filter was shaken in this solution at room temperature for 1 to 2 hours, then washed three times with the aforesaid washing solution and then with a washing solution not containing Tween 20, and then colored with HRP Development Reagent (bio-Rad Company). The results obtained by using 1F12A7 as the purified antibody are shown in FIG. 1. It is clearly seen from this figure that 1F12A7 bound both to the coarsely purified TNF and the purified TNF and thus has the ability to specifically binding to TNF.

By the same procedure, it was confirmed that antibodies 9C4G5, 8E6B6, 10B7E11, 11D7G4, 8E6C6, 2B2H10, 9C4A9, 8E6D7, 1G7D3, 8E6G4, 10B7C6, 9E8G7, 1A10D4, 1F12A9 and P4B4D5 have the ability to specifically binding to TNF.

EXAMPLE 3

Study of the ability to neutralize the TNF's effect of inhibiting fatty acid metabolism:

Mouse fibroblast cells were confluently proliferated and then subjected to induction of differentiation for two days in LMDMEM medium containing 10% bovine fetal serum and 115 micrograms/ml of MIX (3-isobutyl-methyl-xanthine), 395 ng/ml of DEX (dexamethasane) and 10 micrograms/ml of INS (bovine insulin) to differentiate the cells into fat cells. Two days after the induction, the culture medium was replaced by a differentiation maintaining medium (LMDMEM medium containing 10% bovine fetal serum and 50 ng/ml of INS), and a sample was added to 1 to 2 hours later. The sample was TNF added to attain a final concentration of 47 ng/ml, or a product obtained by mixing TNF and an anti-TNF antibody in a molar ratio of 1:1 and incubating the mixture at room temperature for 1 hour which was added so as to attain a TNF concentration of 47 ng/ml. After adding the sample, the mixture was incubated at 37° C. for 4 hours, and then heparin was added so as to attain a final concentration of 10U/ml. The incubation was carried out further for 1 hour. After the incubation, the supernatant was taken out, and the lipoprotein lipase activity in the supernatant was measured by reacting it with ³H-labelled trilein as a substrate. The results are shown in Table 1 below. It is evident from Table 1 that the anti-TNF antibody which can neutralize the cytotoxic effect of TNF on L929 also neutralize the action of TNF to inhibit fatty acid metabolism of 3T3-L1 fat cells. It is also clearly seen from the table that the anti-TNF antibodies which do not neutralize the cytotoxic effect of TNF do not neutralize the action of TNF to inhibit fatty acid metabolism of 3T3-L1 fat cells.

TABLE 1

| Antibody | Ability of neutralizing inhibition of LPL activity (%) |
|---|---|
| Neutralizing antibody | |
| 11D7G4 | 100 |
| 8E6G4 | 67 |
| 9C4A9 | 31 |
| 1G7D3 | 34 |
| Non-neutralizing antibody | |
| 1A10D4 | 0 |
| 1F12A7 | 0 |
| 1F12A9 | 0 |
| 9E8G7 | 0 |
| Mouse IgG | 0 |

EXAMPLE 4

Identification of specific epitopes:

Many peptide fragments having the amino acid sequence of TNF indicated in Table 2 were synthesized using peptide synthesizer 430A of Applied Biol. System Inc. on the basis of the amino acid sequence of a known TNF. After the synthesis, the peptide fragments were disassociated from a supporting resinous structure by treatment with hydrogen fluoride, and subjected to inversephase column chromatography to determine their purities and as required, purified. The peptide fragments having a sufficient degree of purification were used in the experiment.

Each purified peptide fragment (0.5 to 1 mg/ml) was allowed to stand overnight at 4° C. on an immunoassay plate (Titertek) and fixed. The plate was washed three times with a washing solution containing 0.5% bovine serum albumin (20 mM phosphate buffer, 0.136 M NaCl, 0.05% Tween 20, 0.2% NaH$_3$). Then, a buffer containing 1% bovine serum albumin (20 mmM phosphate buffer, 0.135 M NaCl, 0.2% NaN$_3$) was added, and the plate was left to stand at room temperature for 1 to 2 hours. The plate was then washed three times with the aforesaid washing solution. The purified anti-TNF antibody was added and reacted at room temperature for 1 to 2 hours. The plate was washed three times with the aforesaid washing solution, and goat-antimouse IgG-conjugated alkaline phosphatase was added, and the plate was further left to stand at room temperature for 1 to 2 hours. The plate was washed with the aforesaid washing solution and p-nitrophenyl phosphate, disodium, a substrate for the alkaline phosphatase, was added in a concentration of 1 mg/ml. Changes in absorbance per minute at a wavelength of 405 nm were measured by an ELISA analyzer (ETY-86 supplied by Toyo Sokki K. K.).

The reactivity of the antibodies with various peptides was examined by the above method, and the antibodies showed the binding activity shown in Table 3. It was found that the antibodies capable of neutralizing TNF activity specifically bind to a peptide having the following sequences which correspond to the 68th to the 97th of the amino acid sequence of TNF.

NH$_2$-Gly Cys Pro Ser Thr Val Leu Leu Thr His Thr Ile Ser Arg Ile Ala Val Ser Tyr Gln Thr Lys Val Asn Leu Leu Ser Als Ile-COOH.

The three antibodies incapable of neutralizing the activity of TNF (1F12A7, 1F12A9, 9E8G7) bound to the synthetic peptide fragments D and J in Table 2, and thus specifically recognize epitopes contained in the 113th to the 127th amino acid in the amino acid sequence of human tumor necrosis factor, and which is common to the peptides D and J.

NH$_2$-Pro Trp Tyr Glu Pro Ile Tyr Leu Gly Gly Val Phe Gln Leu Glu-COOH.

One antibody (1A10D4) incapable of neutralizing the activity of TNF specifically bound to a peptide having the following sequence corresponding to the 7th to the 37the amino acids in the amino acid sequence of TNF.

NH$_2$-Thr Pro Ser Asp Lys Pro Val Als His Val Val Ala Asn Pro Gln Ala Glu Gly Gln Leu Gln Trp Leu Asn Arg Arg Ala Asn Ala Leu Leu-COOH.

TABLE 2
Synthetic Peptides

A. H$_2$N—Thr Pro Ser Asp Lys Pro Val Ala His Val Val Ala Asn Pro Gln Ala Glu Gly Gln Leu Gln Trp Leu Asn Arg Arg Ala Asn Ala Leu Leu—COOH

B. H$_2$N—Ala Asn Gly Val Glu Leu Arg Asp Asn Gln Leu Val Val Pro Ser Glu Gly Leu Tyr Leu Ile Tyr Ser Gln Val Leu Phe Lys Gly Gln—COOH

C. H$_2$N—Gly Cys Pro Ser Thr His Val Leu Leu Thr His Thr Ile Ser Arg Ile Ala Val Ser Tyr Gln Thr Lys Val Asn Leu Leu Ser Ala Ile—COOH

D. H$_2$N—Lys Ser Pro Cys Gln Arg Glu Thr Pro Glu Gly Ala Glu Ala Lys Pro Trp Tyr Glu Pro Ile Tyr Leu Gly Gly Val Phe Gln Leu Glu—COOH

E. H$_2$N—Lys Gly Asp Arg Leu Ser Ala Glu Ile Asn Arg Pro Asp Tyr Leu Asp Phe Ala Glu Ser Gly Gln Val Tyr Phe Gly Ile Ile Ala Leu—COOH

F. H$_2$N—Ala Asn Ala Leu Leu Ala Asn Gly Val Glu Leu Arg Asp Asn Gln Leu Val—COOH

G. H$_2$N—Gln Val Leu Phe Lys Gly Gln Gly Cys Pro Ser Thr His Val—COOH

H. H$_2$N—Ser Thr His Val Leu Leu Thr His Thr Ile Ser Arg Ile Ala Val Ser—COOH

I. H$_2$N—Ile Ala Val Ser Tyr Gln Thr Lys Val Asn Leu Leu Ser Ala Ile Lys Ser Pro Cys Gln Arg Glu Thr Pro Glu Gly Ala Glu Ala Lys—COOH

J. H$_2$N—Pro Trp Tyr Glu Pro Ile Tyr Leu Gly Gly Val Phe Gln Leu Glu Lys Gly Asp Arg Leu Ser Ala Glu Ile Asn Arg Pro Asp Tyr Leu—COOH

TABLE 3

| | Binding of antibodies to synthetic peptides | | | | | | | | | |
|---|---|---|---|---|---|---|---|---|---|---|
| | A | B | C | D | E | F | G | H | I | J |
| 11D7G4 | 0.4 | 0.3 | 4.1 | 0.5 | 0.3 | 0.2 | 0.1 | 1.6 | 0.3 | 0.5 |
| 9C4G5 | 0.5 | 0.3 | 3.4 | 0.4 | 0.3 | 0.1 | 0.1 | 0.2 | 0.2 | 0.1 |
| 10B7E11 | 0.5 | 0.3 | 2.4 | 0.3 | 0.2 | N.D. | 0.1 | N.D. | 0.1 | N.D. |
| 8E6G4 | 0.3 | 0.2 | 0.8 | 0.2 | 0.1 | N.D. | 0.1 | N.D. | 0.1 | N.D. |
| 8E6B6 | 0.1 | 0.1 | 0.4 | 0.1 | 0.1 | N.D. | N.D. | N.D. | N.D. | N.D. |
| 9C4A9 | 0.2 | 0.1 | 0.5 | 0.2 | 0.0 | N.D. | N.D. | N.D. | N.D. | N.D. |
| 1F12A7 | 0.5 | 0.5 | 5.1 | 44.1 | 2.5 | N.D. | 7.9 | 11.1 | 6.5 | 86.4 |
| 1F12A9 | 2.0 | 0.3 | 1.3 | 34.3 | 2.7 | N.D. | 0.1 | N.D. | 0.2 | N.D. |
| 9E8G7 | 0.6 | 0.1 | 0.4 | 33.0 | 0.1 | N.D. | N.D. | N.D. | N.D. | N.D. |
| 1A10D4 | 28.6 | 0.7 | 1.9 | 4.8 | 0.4 | N.D. | N.D. | N.D. | N.D. | N.D. |

The numerals show the enzyme activity ($\Delta OD_{405}$/min) of the bound labelled antibodies. N.D. indicates that no measurement was done.

To determine the epitopes of TNF to which the antibodies were bound, the following experiment was conducted.

The purified peptide fragment (1microgram/ml) was allowed to stand overnight at 4° C. on an immunoassay plate (Titertek) and fixed. The plate was washed three times with a washing solution containing 0.5% bovine serum albumin (20 mM phosphate buffer, 0.136 M NaCl, 0.05% Tween 20, 0.2% NaN$_3$). Then, a buffer containing 1% bovine serum albumin (20 mM phosphate buffer, 0.135 M NaCl, 0.2% NaN$_3$) was added, and the plate was left to stand at room temperature for 1 to 2 hours. The plate was then washed three times with the aforesaid washing solution. A mixture of the purified anti-TNF antibody and the synthetic peptide, which had been pre-incubated at 37° C. for 1 hour, was added and reacted at room temperature for 1 to 2 hours. The plate was washed three times with the aforesaid washing solution, and goat-antimouse IgG-conjugated alkaline phosphatase was added, and the plate was further left to stand at room temperature for 1 to 2 hours. The plate was washed with the aforesaid washing solution and p-nitrophenyl phosphate, di-sodium, a substrate for the alkaline phosphatase, was added in a concentration of 1 mg/ml. Changes in absorbance per minute at a wavelength of 405 nm were measured by an ELISA analyzer (ETY-86 supplied by Toyo Sokki K. K.).

FIG. 2 shows that the synthetic peptide D (see Table 2) inhibits the binding of the monoclonal antibody 1F12A7 depending upon the dose. The ratio of the antibody bound to THF in the presence of the peptide is shown in FIG. 2 with the amount of the antibody bound to TNF in the absence of the synthetic peptide being taken as 100%. The results demonstrate that the monoclonal antibody 1F12A7 bound to a portion containing the 98th Lys to the 127th Glu of the amino acid sequence of TNF.

EXAMPLE 5

Effect of antibodies on the binding of TNF to TNF receptor:

Using TNF having $^{125}$I introduced thereinto by enzymobeads (Bio-Rad) (specific radioactivity $1.2 \times 10^{10}$ cpm/mg protein), the effect of the anti-TNF antibody on the binding of $^{125}$I-TNF to the TNF receptor on L929 cells. The L929 cells ($3 \times 10^6$ cells) were seeded in a dish and incubated at 37° C. for 4 hours. The supernatant was discarded, and a sample obtained by pre-incubating $^{125}$I-TNF (51 ng/ml) or $^{125}$I-TNF (51 ng/ml) and anti-TNF antibody (5.1 micrograms/ml) at room temperature for 1 hour was added to the cells. On the other hand, to determine the specific binding to the receptor, non-labelled TNF was added to the sample in an amount 100 times as large as the sample was added to the L929 cells, and the mixture was incubated at 37° C.for 2 hours. The cells were collected by a scraper and washed twice with a culture medium (Eagle medium containing 5% bovine fetal serum) by a centrifuging operation. The, the radioactivity of $^{125}$I contained in the cells was measured. As an example of the results, Table 4 below shows the results obtained when anti-TNF antibody 11D7G4 capable of neutralizing the activity of TNF was used. The results clearly show that the anti-TNF antibody 11D7G4 specifically inhibits the binding of TNF to the TNF receptor.

Table 4 also show the results obtained with 1F12A7 incapable of neutralizing the activity of TNF and 10B7E11 capable of inhibiting the binding of TNF to the TNF receptor. These results demonstrate that the anti-TNF antibody 1F12A7 which recognizes epitopes including the 113th to the 127th amino acids of the amino acid sequence of TNF does not at all inhibit the binding of TNF to the TNF receptor.

TABLE 4

| Treatment | Count (cpm) of the specific binding to L929 cells |
|---|---|
| $^{125}$I-TNF (51 ng/ml) | 844.0 ± 151.0 |
| $^{125}$I-TNF (51 ng/ml) + 11D7G4 (5.1 g/ml) | 0 ± 48.2 |
| $^{125}$I-TNF (51 ng/ml) + 10B7E11 (5.1 g/ml) | −18.5 ± 155.6 |
| $^{125}$I-TNF (51 ng/ml) | 860 ± 24.4 |

TABLE 4-continued

| Treatment | Count (cpm) of the specific binding to L929 cells |
|---|---|
| 1F12A7 (5.1 g/ml) $^{125}$I-TNF (51 ng/ml) + mouse IgG (5.1 g/ml) | 837.2 ± 72.2 |

EXAMPLE 6

Preparation of a calibration curve:

The monoclonal antibody "11D7G4" produced in Example 1 was fixed to an insoluble carrier (immunoassay plate) as shown below and used as an antibody in this example. The monoclonal antibody "9C4G5" was labelled with alkaline phosphatase (a produce of Sigma Co.) derived from bovine pancreas and used as a second anti-body.

Figure 3:
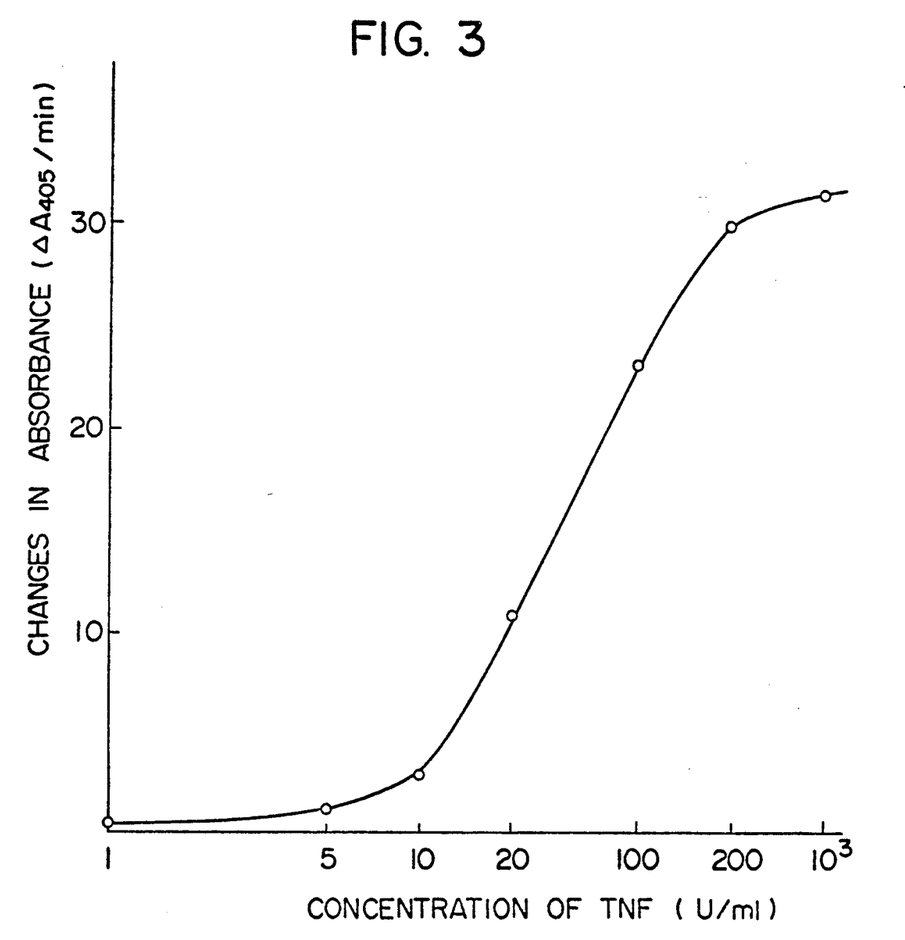
FIG. 3 is a calibration curve for assaying human TNF.

Monoclonal antibody (11D7G4) in a concentration of 15 micrograms/ml was left to stand overnight at 4° C. on an immunoassay plate (Titertek) and fixed. The plate was washed three times with a washing solution containing 0.5% bovine serum albumin (20 mM phosphate buffer, 0.135 M NaCl, 0.05% Tween 20, 0.2% NaN$_3$). Then, a buffer containing 1% bovine serum albumin (20 mM phosphate buffer, 0.135 M NaCl, 0.2% NaN$_3$) was added, and the plate was left to stand at room temperature for 1 hour. It was washed three times with the above washing solution, and then human TNF in various concentrations was added and reacted at room temperature for 1 hour. The plate was washed three times with the above washing solution, and the second antibody (9C4G5) labelled with alkaline phosphatase was added and reacted at room temperature for 1 hour. The plate was washed with the above washing solution, and p-nitrophenyl phosphate, disodium, a substrate for the alkaline phosphatase, was added in a concentration of 1 mg/ml. Changes in absorbance per minute at a wavelength of 405 nm were measured by an ELIZA analyzer (ETY-96). The results are shown in FIG. 3. From this figure, the amount of human TNF can be easily measured by enzyme-linked immunosorbent assay using a monoclonal antibody, which specifically recognizes human TNF, in accordance with the sandwich technique.

EXAMPLE 7

Measurement of TNF in the serum of a Kawasaki disease patient:

Serum taken from a patient of Kawasaki disease, and as controls the serum of a normal healthy person and the serum of a patient of another disease were each diluted to 2 to 10 times with a phosphate buffer (20 mM phosphate buffer, 0.135 M NaCl, pH 7.2) and used as antigens. The amount of TNS in these samples was measured by the sandwich method described in Example 6. Calibration curves used were prepared simultaneously under the same conditions.

Figure 4:
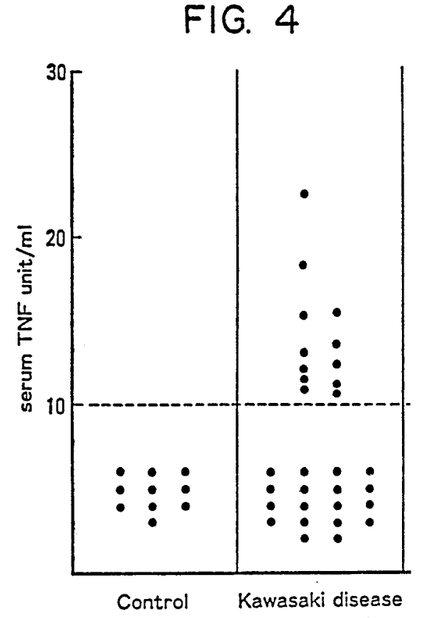
FIG. 4 shows the results of measurement of the amounts of TNF in a serum sample of a patient of Kawasaki disease and a healthy human subject (TNF)
Figure 5:
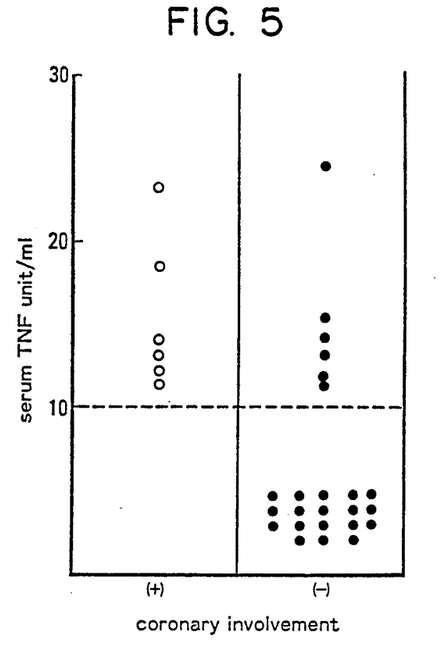
FIG. 5 shows the relation between the serum TNF level and the appearance of coronary involvement.
Figure 6:
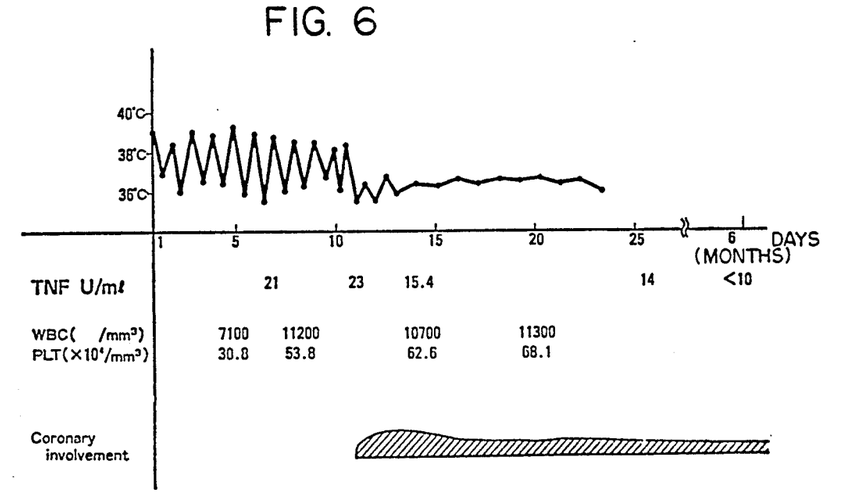
FIG. 6 shows the fever pattern, change of the number of white blood cells (WBC), of the number of platelets (PLT) and of the TNF content in a patient with Kawasaki disease and the appearance of a diseased change in coronary artery.

The results are shown in FIG. 4. TNF was detected from the serum samples of 21 patients (40%) out of 30 patients. As shown in FIG. 5, the detection of TNF is significantly related to the occurrence of a diseased change in coronary artery. As FIG. 6 shows, TNF was well detected in the acute stage of a patient with great severity.

Measurement of the amount of TNF by using the detection kit of this invention is very effective for diagnosing Kawasaki disease and analyzing its condition, especially for the anticipatory diagnosis of the occurrence of a diseased condition in the coronary artery.

EXAMPLE 8

Measurement of TNF in the serum of a patient with a bacterial infection:

The serum of a patient of sepsis from Krebsiella and as controls, the serum of a normal healthy person and as controls, the serum of a normal healthy person and the serum of a patient of another disease were each diluted to 2 to 10 times with a phosphate buffer (20 mM phosphate buffer, 0.135 M NaCl, pH 7.2) and the concentration of TNF in it was measured. The amount of TNF in the serum samples was measured by the sandwich method described in Example 6. Calibration curves used were prepared simultaneously under the same conditions. The results are summarized in Table 5.

The results demonstrate that the amount of TNF in the serum of the patient correlates very well with the amount of white blood cells, the number of platelets, and changes in the amount of C reactive protein, and the severity of the infection is highly related to the amount of TNF. Accordingly, measurement of TNF by using the detection kit of the invention is very effective for diagnosing bacterial infections and analyzing the diseased conditions.

TABLE 5

| Sample No | Concentration of TNF (U/ml) | Number of white blood cells (per mm³) | Number of platelets (×10⁴/mm³) | C reactive protein | Case |
| --- | --- | --- | --- | --- | --- |
| 1 | 108 | not measured | not measured | not measured | sepsis |
| 2 | 250 | 27700 | 1.8 | 22.2 | sepsis |
| 3 | 75 | 21800 | 0.6 | 19.7 | sepsis |
| 4 | not detected | 14800 | 1.7 | 2.7 | sepsis |
| 5 | not detected | 16200 | 11.5 | not detected | sepsis |
| 6 | not detected | 9300 | 36.0 | not detected | sepsis |
| 7 | not detected | not measured | not measured | not measured | normal healthy person |

What we claim is:

1. A method for confirming a diagnosis of Kawasaki disease in a patient comprising
    contacting an anti-tumor necrosis factor antibody with a sample of body fluid from the patient.
    detecting an amount of a substance which specifically binds the anti-tumor factor antibody, and
    comparing the amount of the substance with that in a sample of body fluid taken from a normal, healthy person
    wherein elevated levels of the substance are indicative of Kawasaki disease.
2. The method of claim 1 wherein the anti-tumor necrosis factor antibody is an anti-human tumor necrosis factor monoclonal antibody.
3. The method of claim 2 wherein the anti-tumor necrosis factor monoclonal antibody is capable of
    (a) neutralizing the cytotoxic effect of human tumor necrosis factor on L929 cells and the inhibitory effect of human tumor necrosis factor on fatty acid metabolism,
    (b) recognizing epitopes contained in the 68th (Gly) to the 97th (Ile) amino acids in the amino acid sequence of human tumor necrosis factor, and
    (c) specifically inhibiting binding of human tumor necrosis factor to a tumor necrosis factor receptor.
4. The method of claim 1 comprising
    (a) contacting the body fluid sample with a first anti-tumor necrosis factor antibody immobilized on a solid support, then contacting the solid support with a labelled second anti-tumor necrosis factor antibody, or
    (b) contacting the immobilized first anti-tumor necrosis factor antibody, the labelled second anti-tumor necrosis factor antibody and the body fluid sample simultaneously, and
    detecting the amount of the substance which specifically binds anti-tumor necrosis factor antibody by detecting the amount of bound labelled antibody.
5. The method of claim 1 wherein the body fluid is serum or plasma taken from the patient.

* * * * *